Figure 1:
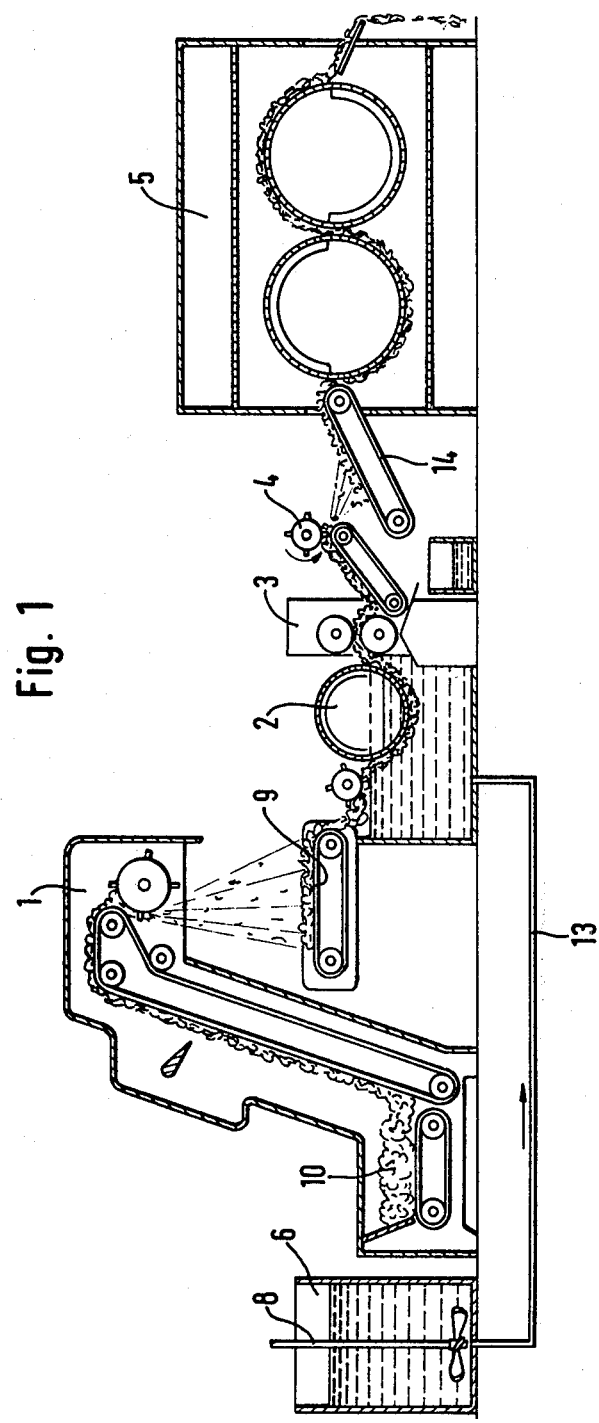

United States Patent [19]

Lask et al.

[11] 4,250,306

[45] Feb. 10, 1981

[54] PROCESS AND EQUIPMENT FOR PREPARING SWELLABLE CROSS-LINKED CARBOXYALKYLCELLULOSES FROM NATURAL CELLULOSE OR CELLULOSE HYDRATE AND USE THEREOF

[75] Inventors: Helmut Lask; Arno Holst, both of Wiesbaden; Ehrenfried Nischwitz, Schmitten-Oberreifenberg; Hans Sommer, Hofheim, all of Fed. Rep. of Germany

[73] Assignee: Hoechst Aktiengesellschaft, Fed. Rep. of Germany

[21] Appl. No.: 43,172

[22] Filed: May 29, 1979

[30] Foreign Application Priority Data

May 31, 1978 [DE] Fed. Rep. of Germany ....... 2823736

[51] Int. Cl.$^3$ ..................... C08B 15/10; D04H 1/42
[52] U.S. Cl. ................... 536/88; 68/DIG. 5;
536/85; 536/87; 536/98
[58] Field of Search ............ 536/88, 85, 87, 98;
68/DIG. 5

[56] References Cited

U.S. PATENT DOCUMENTS

| | | | |
|---|---|---|---|
| 2,145,862 | 2/1939 | Collings et al. | 536/84 |
| 2,553,725 | 5/1951 | Rogers et al. | 536/85 |
| 2,879,607 | 3/1959 | Fleissner et al. | 68/DIG. 5 |
| 3,589,364 | 6/1971 | Dean | 427/180 |
| 3,928,920 | 12/1975 | Fleissner | 68/DIG. 5 |
| 3,997,647 | 12/1976 | Lassen | 428/393 |
| 4,066,828 | 1/1978 | Holst et al. | 536/88 |
| 4,068,067 | 1/1978 | Holst et al. | 536/88 |
| 4,068,068 | 1/1978 | Holst et al. | 536/88 |
| 4,075,279 | 2/1978 | Holst et al. | 536/88 |
| 4,097,667 | 6/1978 | Holst et al. | 536/87 |

FOREIGN PATENT DOCUMENTS 1492040  11/1977  United Kingdom .

OTHER PUBLICATIONS

Chemical Abstracts, vol. 85, No. 2, Jul. 12, 1976, p. 7217q.
Chemical Abstracts, vol. 86, No. 26, Jun. 27, 1977, p. 191581y.

Primary Examiner—Ronald W. Griffin
Attorney, Agent, or Firm—James E. Bryan

[57] ABSTRACT

This invention relates to a process for preparing swellable cross-linked carboxyalkylcelluloses by reacting cellulose, a carboxyalkylating etherifying agent, and a cross-linking agent in an aqueous alkaline medium, comprising effecting alkalizing, etherifying, and cross-linking simultaneously in one reaction step using fibers, textile sheet materials containing these fibers, or sheet materials of other kinds, having a base of cellulose hydrate or of natural cellulose, by contacting said fibers or sheet materials with an ample quantity of an aqueous alkaline reaction mixture, removing part of the reaction mixture from the fibers or sheet materials contacted therewith, so that at least the quantity required for reaction is still present, and treating the fibers or sheet materials containing the remainder of the aqueous alkaline reaction mixture with heat energy. The invention also relates to equipment for performing the process.

11 Claims, 2 Drawing Figures

PROCESS AND EQUIPMENT FOR PREPARING SWELLABLE CROSS-LINKED CARBOXYALKYLCELLULOSES FROM NATURAL CELLULOSE OR CELLULOSE HYDRATE AND USE THEREOF

The present invention relates to a process for preparing swellable cross-linked carboxyalkylcelluloses from natural cellulose or cellulose hydrate, to equipment for carrying out a process of this type, and to the use of products so prepared, particularly in the manufacture of non-woven fabrics.

Recently, swellable carbohydrate derivatives, for example, swellable cross-linked cellulose ethers, particularly carboxyalkylcelluloses, have increasingly gained significance in all fields in which physiological fluids, for example, urine, blood, perspiration, or saliva must be absorbed, namely in infant care, female hygiene, and for the purposes of medical practices and hospitals. They are either incorporated as additions in the absorptive compositions used, e.g., in tampons, sanitary pads, non-woven fabrics, baby's napkins, or under-blankets, which frequently have cellulose as a base material, or they are the sole constituents of these compositions.

Further, these swellable substances are used to improve the absorption capacity for water vapor of binder-treated non-woven fabrics which are of interest for various technical applications. These applications include the use of the non-woven fabrics as substitutes, particularly for leather or certain textiles which are, for example, employed in the manufacture of shoes (shoe uppers, linings, soles), bags, upholstery covers, outer garments ("leather" and all-weather garments) or for textiles and articles for domestic use (table cloths, window "leathers", wiping cloths). They are, however, also used in combination with or as complements to the materials (e.g. leather or textiles) which may be employed for the above-mentioned purposes, apart from the non-woven fabrics.

Other possible applications for these swellable substances are in the manufacture of sheet materials which are capable of absorbing and transmitting water vapor and are prepared from various natural or synthetic polymers, for example, polyvinyl chloride, polyurethane, rubber, polyalkylenes, cellulose hydrate etc. These sheet materials which may have, for example, the form of self-supporting films or of coatings on substrates are, particularly, suitable as leather substitutes (synthetic leather) for use as shoe uppers, upholstery covers, bags, and outer garments ("leather" and all-weather garments), or as covering materials, e.g., tent materials or tarpaulins.

Various processes are known for preparing swellable carbohydrate derivatives, e.g., swellable cross-linked cellulose ethers. Among these are, especially, the following: German Offenlegungsschrift No. 1,912,740 (corresponding to U.S. Pat. No. 3,589,364) describes carboxymethylcellulose fibers which are suitable for use in fiber materials absorbing and retaining aqueous solutions and which are substantially insoluble in water. They are wet-cross-linked fibers of originally water-soluble salts of carboxymethylcellulose (CMC) having a degree of substitution (DS) of about 0.4 to 1.6, and they have the original structure of the cellulose fibers. They are prepared either in a single reaction step in which the cellulose is simultaneously carboxymethylated and wet-cross-linked, or in two reaction steps in which the cellulose is first wet-cross-linked and then carboxymethylated. The initial substance used for the reaction is natural or regenerated cellulose; the cross-linking agent is caused to act under alkaline or acid conditions. Among the various cross-linking agents, epichlorohydrin is preferred. The cellulose fibers are suspended in an inert organic diluent, for example, isopropanol, in the presence of a small amount of water, and are caused to react under alkaline conditions with about 3 to 10% by weight of the cross-linking agent. The amount of the inert organic diluent used corresponds to about 40 times the amount of cellulose.

German Offenlegungsschrift No. 2,364,628 discloses a structure, rendered hydrophilic, of a fiber-forming and a film-forming water-insoluble polymer, which contains particles of modified cellulose ethers which are such that if only etherification were carried out to the given extent, water-soluble cellulose ethers would result, but which are modified in such a way that, at least for the major part, they are water-insoluble but retain the capacity to absorb water. The structures, rendered hydrophilic, are, particularly, films but also filaments, provided they are prepared in a usual precipitation process, e.g., from regenerated cellulose. The pulverulent or granular material composed of the modified cellulose ethers is, for example, added to the polymer composition and is uniformly distributed therein prior to forming.

A process for improving the absorption of water and the absorptivity of fiber materials composed of or containing synthetic fibers or filaments is described in German Offenlegungsschrift No. 2,441,781. In this process, modified highly-absorbent cellulose ethers are fixed to the fiber materials with the aid of finishing agents, permanent-finishing agents, resins, or binders. The modified cellulose ethers are, together with the agents serving to fix them to the fiber material, applied to the latter from aqueous preparations, such as solutions, dispersions, or emulsions. A cellulose ether modified with N-methylol acrylamide is preferably used, in an amount of about 0.1 to 5% relative to the weight of the improved fiber material.

In the process for the preparation of highly-absorbent cellulose filaments according to German Offenlegungsschrift No. 2,447,282 (corresponding to U.S. Pat. No. 3,997,647) modified cellulose fibers are caused to swell in a liquid, so that they can be extruded in the swollen condition; during extrusion the fibers are oriented, and they combine to form filaments. The filaments are then dried to neutralize the swollen intermediate condition of the fibers and to allow the formation of capillary-type longitudinal channels within the filaments. By "modification of the cellulose" a chemical substitution, a chemical substitution and cross-linking, or a graph-polymerization is to be understood.

German Offenlegungsschrift No. 2,519,927 (corresponding to U.S. Pat. No. 4,068,068) discloses a process for the preparation of cellulose ethers which absorb water, but are to a large extent insoluble in water. In this process, cellulose is, in the presence of an alkali, reacted with an etherifying agent in such a way that a water-soluble cellulose ether would result, if etherification only were carried out. Prior to, simultaneously with, or after etherification of the cellulose cross-linking with bisacrylamido-acetic acid is effected. The cellulose is alkalized in a first step, and in a second, and if necessary in a third step, the other reaction components are, successively or together, added to the alkali cellulose in the presence of 0.8 to 7.5 parts by weight of isopropanol, relative to the weight of the cellulose, and are caused to react for about 1 hour at a temperature of about 50° to 80° C. The last-mentioned reaction also may be performed directly with the alkali-cellulose which is moist with water, without the addition of isopropanol, provided the existing mixture of powder or crumbs is loose and does not stick together.

A similar way of carrying out the reaction without any organic diluent also has been disclosed in German Offenlegungsschrift No. 2,520,337 (corresponding to U.S. Pat. No. 4,066,828). The cross-linking agents used are acrylamidomethylene chloroacetamide, dichloroacetic acid, phosphorus oxychloride, or compounds of a type, which as groups which are reactive towards cellulose in alkaline media, contain at least two of the acrylamido group, the chloroazomethine group, or the allyloxyazomethine group.

German Offenlgungsschrift No. 2,543,187 describes another method of effecting the reaction without any organic diluent. In this method, clippings from lacquered or unlacquered cellulose hydrate films are alkalized in a first step, and are then etherified using a halogen fatty acid, for example, monochloro-acetic acid, and reacted with a polyfunctional cross-linking agent.

German Offenlegungsschrift No. 2,710,874 describes a process in which rayon staple fibers are placed in a reactor equipped with a pump circulating system for solvents and are alkalized with an about 50% concentration aqueous NaOH solution, in the presence of about 13 parts by weight of an 87% concentration isopropanol per part by weight of fibers. Then the alkalized rayon stable fibers are etherified with Na-monochloroacetate and simultaneously cross-linked with bisacrylamidoacetic acid for about 1 hour at a temperature of about 70° C. Upon completion of the reaction the mixture is neutralized and filtered, and the solid residue composed of cross-linked etherified rayon staple fibers is washed free from salt in an aqueous alcohol. The fiber material obtained has a good absorption and retention capacity for water and is water-insoluble to the extent of about 70%.

The processes known from prior art have, however, various disadvantages:

In all preparation processes, alkalizing is carried out separately and, thus, in a time-consuming manner, prior to the etherifying and/or cross-linking reaction.

The more or less important quantities of organic diluents used require expensive special apparatus in order to recover these diluents or to reprocess them in an ecologically acceptable way, and also to meet the stringent requirements with respect to the operational safety of the processes in which these diluents are employed.

In the processes which are carried out without adding any organic diluents the course of the reaction is often very irregular, because the mixture of powder or crumbs used makes it difficult for the reaction components to reach all reactive areas of the cellulosic material.

The application of absorbent modified cellulose ethers or similar substances to the surfaces of fibers, or the incorporation of these substances in the raw material mass used for preparing the fibers, often renders difficult the further processing of the components brought together. In addition, it is inconvenient that the absorbing capacity of the modified cellulose ethers added is reduced either by the auxiliary agents used to facilitate the application, or during the fiber production from the component mixture.

The preparation of fibers and/or filaments directly from modified cellulose derivatives normally can be carried out only using cellulose derivatives which are not too highly swellable, because otherwise the fiber and/or filament production is rendered difficult by the swelling liquids.

It is, therefore, an object of the present invention to provide a process and an equipment for preparing cross-linked carboxyalkylcelluloses which do not require a great amount of expensive apparatus and provide fibers, textile sheet materials containing these fibers, or sheet materials of other kinds, which have a base of natural cellulose or of cellulose hydrate and exhibit a good swelling capacity.

The invention is based on the process for preparing swellable cross-linked carboxyalkylcelluloses by reacting cellulose, a carboxyalkylating etherifying agent, and a cross-linking agent in an aqueous alkaline medium. The process of the invention has the feature that alkalizing, etherifying and cross-linking are carried out simultaneously in one reaction step using fibers, textile sheet materials containing these fibers or sheet materials of other kinds, which have a base of cellulose hydrate or of natural cellulose. The fibers or the sheet materials are first brought into contact with an ample quantity of an aqueous alkaline reaction mixture, then part of the reaction mixture is removed again from the fibers or sheet materials contacted therewith, so that at least the quantity required for reaction is still present, and the fibers or sheet materials containing the remainder of the aqueous alkaline reaction mixture are treated with heat energy.

Swellable carboxyalkylcelluloses are those which swell when they are immersed in aqueous liquids, particularly liquids containing more than 50% by weight of water, or when they come, in another way, into contact with water molecules (for example water vapor); they are water-insoluble to the extent of at least about 30% by weight, particularly, of at least about 50% by weight. The carboxyalkylcelluloses prepared according to the present invention are either in the form of fibers having lengths of about 0.1 mm to about 200 mm, particularly of about 1 mm to about 150 mm, if a fiberform starting material is used, or they are in the form of sheet materials, if the starting material is a film or a sponge cloth.

The process of the invention is, especially, carried out in such a way that the fibers of natural cellulose or of cellulose hydrate or the sheet materials containing these fibers are sprayed with or immersed in the aqueous alkaline reaction mixture which contains the aqueous solution of an alkalizing agent and, in addition, already the carboxyalkylating etherifying agent and the cross-linking agent. This process step is, among others, carried out to achieve a good mixing of the fibers or sheet materials with the reaction mixture, because producing a uniform contact between the fibers or the sheet materials and the other reaction components will yield the advantage of a uniform course of the reaction, i.e. an as far as possible homogeneous substitution on the cellulose molecules can be obtained.

For the purpose of the actual chemical reaction the excess quantity of the reaction mixture is removed again from the fibers or sheet materials contacted therewith. This may, particularly, be done by squeezing off or centrifuging. The excess quantity is maximally the quantity which is not required for the chemical reaction of the cellulose with the aqueous mixture composed of the alkalizing, etherifying, and cross-linking agents; appropriately, it amounts to a multiple of the quantity which is actually needed for the reaction, for example, 5 to 50 times the quantity. To effect the chemical reaction between the participants in the reaction the mixture composed of the fibers or sheet materials and the remainder of the reaction mixture is treated with heat energy. Heat energy is appropriately applied in the form of hot air, for example, in a drying apparatus (e.g. a drying chamber) equipped with an air circulating system, or in another type of equipment in which hot air or superheated steam streams through the material to be treated; or heat energy is generated by means of microwaves. If microwaves are employed heat is not applied from the outside, as in the case of the other process variants mentioned, but is generated directly on the fibers or sheet materials, i.e. at the place of the actual chemical reaction.

The required reaction times depend, among others, upon the transmission of heat through the fibers or sheet materials, that is to say, the better the heat transfer, the shorter the reaction time. The required reaction times range between about 15 seconds and about 60 minutes, depending upon the way in which heat energy is supplied. If hot air or superheated steam is used, the reaction time ranges, for example, preferably from about 1 minute to about 10 minutes, at a temperature of the hot air of about 70° C. to about 160° C. If, on the other hand microwaves are employed, the reaction time ranges from about 15 seconds to about 60 seconds.

For economic reasons, an aqueous NaOH solution is nearly always used as the alkalizing agent for the natural cellulose or the cellulose hydrate when carrying out the process of the invention. Other aqueous alkaline solutions, for example, KOH or LiOH solutions, are, however, also suitable as alkalizing agents. The concentrations of the aqueous solutions may vary within wide limits, appropriately they range from about 10 to 60% by weight.

As the carboxyalkylating etherifying agents monochloroacetic acid or the salts thereof are preferred; but monochloropropionic acid or acrylamide may also be used, and then the carboxyalkylation is a carboxyethylation or, preferably, a carboxymethylation and results in a carboxymethyl cellulose (CMC) or a carboxyethyl cellulose (CEC). If the process of the invention were carried out without the mandatory cross-linking, the degrees of substitution (DS) of the resulting cellulose ethers would be such that the latter would be at least partially water-soluble.

Apart from the etherifying reaction, cross-linking is carried out in the process according to the invention, and cross-linking results in products which absorb comparatively large quantities of water and are also capable of retaining these quantities more or less well, without dissolving completely themselves. The below-mentioned cross-linking agents are preferred for this purpose; of these, particularly, 0.0005 to 0.2 part by weight should be used, relative to 1 part by weight of the natural cellulose or the cellulose hydrate. They are compounds carrying at least one of the following functional groups reactive towards hydroxyl groups:

the acrylamido group, $R_1$ being H or $CH_3$ 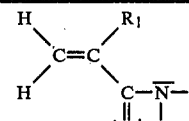

an α halogenoepoxy group, Hal being Cl or Br 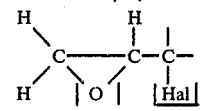

the chloroazomethine group 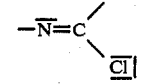

and the allyloxy-azomethine group 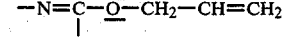

The cross-linking agent also may be phosphorus oxychloride or acrylamido-methylene chloroacetamide. Dichloro-acetic acid which also may be employed as a cross-linking agent should, however, be used in a quantity of at least 0.01 part by weight per part by weight of the natural cellulose or of the cellulose hydrate.

The following are exemplary of compounds carrying the functional groups mentioned:
methylene bisacrylamide,
bisacrylamido-acetic acid,
N,N'-dimethylol-methylene-bisacrylamide,
1,1-bisacrylamido-ethane,
methylene-bismethacrylamide,
epichlorohydrin,
2,4,6-trichloro-pyrimidine,
2,4,5,6 tetrachloro-pyrimidine,
cyanuric chloride,
triallyl-cyanurate.

The cellulosic starting materials used in the process of the invention may be, on the one hand, composed of fibers of a natural cellulose, which are, for example, prepared from the fibrocellules of more highly developed plants, e.g., from cotton, bast, leaf, wood, and grass fibers (e.g. cereal straw, bamboo, sugar cane waste), including, among others, raw cotton, cotton linters, pulp, ramie, flax, or hemp. The natural cellulose fibers, however, also may be in the form of a finished textile sheet material, for example, a woven or a non-woven fabric, in which these fibers may not only be exclusively present, but also may be blended with other fibers, for example, fibers of cellulose hydrate or synthetic fibers, such as polyester fibers.

On the other hand, the cellulosic starting materials used may be fibers or sheet materials, such as films or sponge cloths, of cellulose hydrate, i.e. fibers, films or sponge cloths of regenerated cellulose (for example, viscose, i.e. fibers, films or sponge cloths prepared from cellulose sodium xanthogenate in precipitating baths). Preferably, so-called rayon stable fibers are used, i.e. fibers of cellulose hydrate which have been cut as uniformly as possible and have lengths ranging from about 30 to about 150 mm, particularly from about 30 to about 60 mm. The cellulose hydrate fibers may, however, also be in the form of a finished textile sheet material, for example, a woven or a non-woven fabric, in which these fibers may not only be exclusively present, but also may be blended with other fibers, for example, fibers of a natural cellulose, such as cotton, or synthetic fibers, such as polyester fibers.

Appropriately, the molar relationships of the components to be used in the process according to the invention range from about 0.7 to 2.1 moles of alkali hydroxide, 10 to 30 moles of $H_2O$, 0.7 to 2 moles of the etherifying agent, and 0.005 to 0.1 mole of the cross-linking agent (relative to 1 mole of cellulose).

The aforementioned object is further obtained by equipment for carrying out a process for preparing swellable cross-linked carboxyalkylcelluloses by reacting cellulose, a carboxyalkylating etherifying agent and a cross-linking agent in an aqueous alkaline medium, as described above. The equipment according to the invention has the following features:

(a) a unit for preparing and storing the aqueous alkaline reaction mixture, (b) a unit for contacting fibers, textile sheet materials containing these fibers, or sheet materials of other kinds having a base of cellulose hydrate or of natural cellulose with an ample quantity of the aqueous alkaline reaction mixture, (c) a unit for removing the reaction mixture from the fibers or sheet materials contacted therewith, so that at least the quantity required for reaction is still present, (d) a unit for treating with heat energy the fibers or sheet materials containing the remainder of the aqueous alkaline reaction mixture, and connecting elements between units a to d.

With the aid of the equipment according to the invention the process of the invention may be performed either discontinuously or, particularly, continuously, if the required reaction components are continuously fed into and discharged from unit b.

Figure 2:
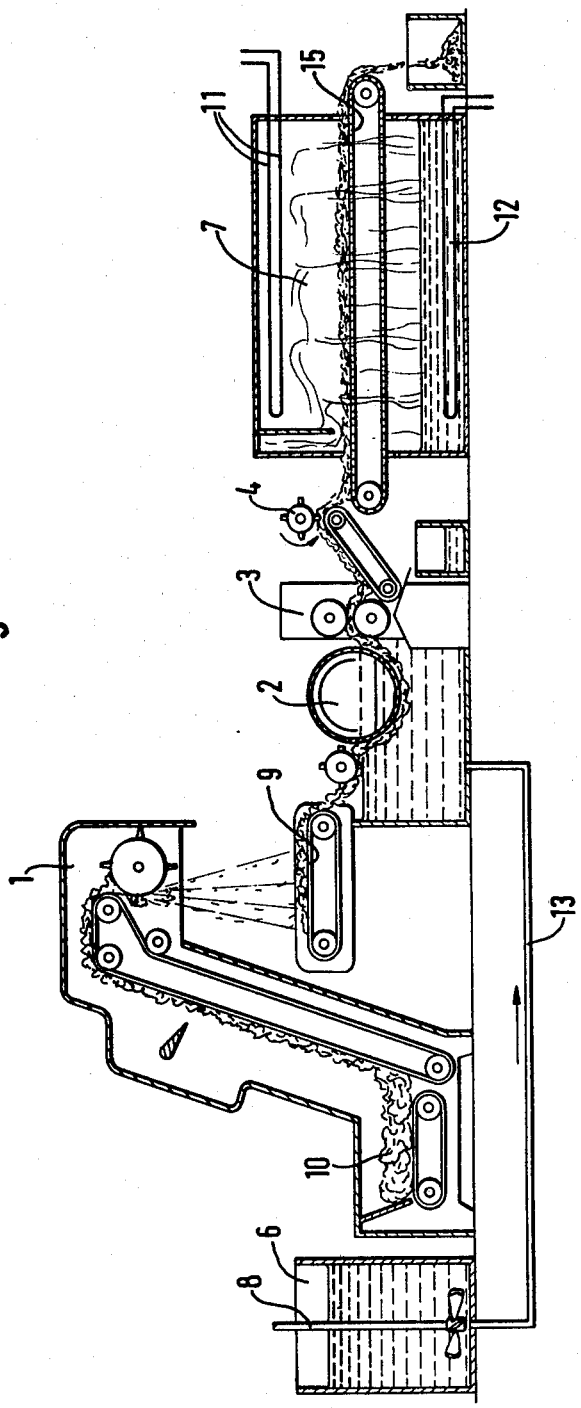

Two embodiments of the equipment according to the invention are diagrammatically shown in FIGS. 1 and 2 of the accompanying drawings.

According to FIG. 1, the fibers which may, for example, be in the form of flocks 10 are fed into a pretreating unit, e.g., a hopper feeder 1 wherein the flocks are opened up several times; via a conveyor belt 9 the fibers are then fed into the unit b, particularly a sieve drum washer 2 which is filled and refilled with the reaction mixture via a feed line 13 connecting it with unit a, e.g. a tank 6 equipped with an agitator 8. The fibers which are moistened with an ample quantity of the reaction mixture are freed again from parts of the reaction mixture in the unit c, e.g., a padder 3, until at least the quantity required for reaction is still present. Following the squeezing operation in the unit c, the squeezed off fibers are loosened again in a post-treating device, e.g., an unravelling machine 4, in order to facilitate the subsequent reaction. The fibers containing the remainder of the aqueous alkaline reaction mixture are, via a conveyor belt 14 fed into the unit d, particularly a sieve drum drier 5, wherein they are treated with hot air.

FIG. 2 shows another preferred embodiment of unit d which also may be a sieve belt steamer 7, wherein the fibers, while being transported over a sieve belt 15, are treated with hot or superheated steam produced from water contained in the unit 12 with the aid of heating coils; this sieve belt drier also may be equipped with additional heating coils 11 arranged at the top. The fibers discharged from the unit d have been cross-linked and etherified to the above-specified extent and have, thus, become swellable.

If the cellulosic starting material is not in the form of fibers, but, e.g., in the form of a woven fabric, a non-woven fabric, a blended woven fabric, a blended non-woven fabric, a sponge cloth, or a film, the devices 1 and 4 are not required in the equipment of the invention, as it is unnecessary or impossible to open up or loosen these starting materials.

The process and the equipment of the invention enable a technologically simple preparation of the products, because there is, for example, no need for explosion-proof equipment parts. In addition, the reaction time may be reduced, because the process allows a combination of alkalizing, etherifying, and cross-linking in one reaction step. By contacting the fibers or sheet materials with considerable quantities of the reaction mixture a good reaction behavior is ensured; the actual chemical reaction is then carried out with the required quantity of the reaction mixture only. Among others, it is thus possible to save energy and to use equipment which is not excessively large.

The fibers or sheet materials prepared according to the process of the invention are, especially, used in the production of non-woven fabrics. The other aforementioned applications are, however, also feasible. Further details with respect to the incorporation of, particularly, swellable fibers in non-woven fabrics or sheet materials having a base of polymer compositions are disclosed in the following publications:

German Offenlegungsschriften Nos. 2,756,671 (incorporation in polyurethane), 2,756,484 (incorporation in polyvinyl chloride), 2,710,874 (incorporation in non-woven fabrics), 2,736,205 (incorporation in rubber), and 2,736,147 (incorporation in adhesives).

The parameters used in the description and in the examples to characterize the carboxyalkylcelluloses prepared according to the invention are defined as follows:

WRV: Water retention value of the swellable cross-linked polymer in % by weight, measured against 1,600 times the acceleration due to gravity, relative to its water-insoluble fraction; WRV is determined after immersing the sample in water.

WUA: Water-insoluble fraction in the swellable cross-linked polymer.

DS: Degree of substitution, i.e. the average number of substituted hydroxyl groups on the anhydro-α-glucose units, from 0.0 to 3.0

EXAMPLE 1

The required reaction mixture is prepared as follows: 42.5 kg of NaOH are added to 325 kg of $H_2O$ while stirring, and when the aqueous NaOH solution has cooled down, first 10.5 kg of bisacrylamido-acetic acid and then 123 kg of Na-monochloroacetate are added. Rayon staple fibers (1.7 dtex, length 40 mm) which have been opened up three times in the hopper feeder are added to this reaction mixture in the sieve drum washer, and the fibers saturated with the reaction mixture are then squeezed off in the padder in such a way that 100 g of untreated fibers weigh 300 g prior to carrying out the actual chemical reaction, i.e. 100 g of the fiber material contain 200 g of the reaction mixture. After the fiber material again has been opened up in an unravelling machine, it is passed through a sieve drum drier where the actual chemical reaction takes place; the temperature in the drier is 105° C., and the fibers stay in the drier for 2.75 minutes. Following neutralizing in glacial acetic acid and washing the reaction product in water and 100% isopropanol, the fiber material, if desired, may be conditioned, for example, using the 0.3% concentration conditioning agent ® Leomin HSG (a fatty acid polyglycol ester) manufactured by Hoechst AG. The dried fibers have the following parameters:

WRV=500, WUA=93, and DS=0.2

EXAMPLE 2

The procedure is the same as in Example 1, but chemical reaction is carried out in a sieve belt steamer; the temperature in the steamer is 100° C.; the fibers stay in the steamer for 3 minutes. The dried fibers have the following parameters:

WRV=600, WUA=92.5, and DS=0.21.

EXAMPLE 3

The procedure is the same as in Example 1, but the reaction mixture contains only 4.2 kg of bisacrylamidoacetic acid, and the fibers are squeezed off in such a way that 100 g of the untreated fiber material contain 170 g of the reaction mixture. The reaction is carried out in the sieve drum drier at 95° C. and during a stay of the fibers in the drier of 1.5 minutes. After neutralizing in glacial acetic acid, washing the reaction product in a 70% aqueous isopropanol, and drying, the fibers have the following parameters:

WRV=3,277, WUA=51.7 and DS=0.43.

EXAMPLE 4

A sponge cloth prepared from cellulose hydrate (weight per unit area 250 g/m$^2$) is reeled off of a roll directly into the sieve drum washer and is treated according to Example 3; squeezing off is effected in such a way that 100 g of the untreated sponge cloth contain 220 g of the reaction mixture. The saturated and then squeezed off sponge cloth is not opened up, but is directly fed into the sieve drum drier and reacted at 95° C. for 1.5 minutes. After neutralizing in glacial acetic acid, washing in 70% aqueous isopropanol, and drying, the sponge cloth has the following parameters:

WRV=580 (untreated sponge cloth: 102), WUA=84.5, and DS=0.28.

EXAMPLE 5

The procedure is the same as in Example 3, but in this case a defibrillized pine sulfite pulp is used as the starting material and squeezing off is effected in such a way that 100 g of pulp contain 200 g of the reaction mixture. By means of the unravelling machine, a uniform, about 1 cm thick layer is fed into the sieve drum drier and caused to react at 95° C. for 2 minutes. The dried pulp has the following parameters:

WRV=408, WUA=80.8, and DS=0.26.

EXAMPLE 6

The procedure is the same as in Example 3, but in this case a cotton fabric is used as the starting material which is not opened up. The reaction is carried out in the sieve drum drier at 95° C. for 2 minutes. The dried fabric has the following parameters:

WRV=350 (untreated fabric: 90), WUA=95, and DS=0.18.

It will be obvious to those skilled in the art that many modifications may be made within the scope of the present invention without departing from the spirit thereof, and the invention includes all such modifications.

What is claimed is:

1. A process for preparing swellable cross-linked carboxyalkylcelluloses by reacting cellulose, a carboxyalkylating etherifying agent, and a cross-linking agent in an aqueous alkaline medium, comprising effecting alkalizing, etherifying, and cross-linking simultaneously in one reaction step using fibers, textile sheet materials containing these fibers having a base of cellulose hydrate or of natural cellulose, or sheet materials from the group of films and sponge cloths composed of cellulose hydrate, by contacting
   (a) said fibers or sheet materials with an ample quantity of an aqueous alkaline reaction mixture,
   (b) removing part of the reaction mixture from the fibers or sheet materials contacted therewith, so that at least the quantity required for reaction is still present, wherein the molar relationships of the components of said quantity of the reaction mixture ranges, relative to 1 mole of cellulose, from 0.7 to 2.1 moles of alkali hydroxide, 10 to 30 moles of $H_2O$, 0.7 to 2 moles of the etherifying agent and 0.005 to 0.1 mole of the cross-linking agent, and
   (c) treating the fibers or sheet materials containing said remainder of the aqueous alkaline reaction mixture with heat energy for the purpose of the actual chemical reaction.

2. A process according to claim 1 in which the etherification is a carboxymethylation with monochloroacetic acid or the salts thereof.

3. A process according to claim 1 in which the cross-linking is a reaction with phosphorus oxychloride, acrylamidomethylenechloroacetamide or with a compound which carries at least one of the following functional groups reactive towards hydroxyl groups:

| | |
|---|---|
| the acrylamido group, $R_1$ being H or $CH_3$ | 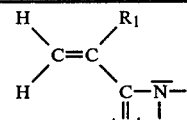 |
| an α halogenoepoxy group, Hal being Cl or Br | 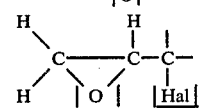 |
| the chloroazomethine group | 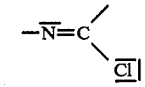 |
| and the allyloxy-azomethine group | 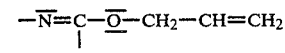 |

4. A process according to claim 1 in which the fibers or the sheet materials are contacted with the aqueous alkaline reaction mixture by spraying or immersing.

5. A process according to claim 1 in which the excess quantity of the reaction mixture is removed from the fibers or the sheet materials by squeezing off or centrifuging.

6. A process according to claim 1 in which the final reaction between the fibers or the sheet materials and the reaction mixture, heat energy is applied in the form of hot air or steam or by a treatment with microwaves.

7. A process according to claim 1 in which the fibers used are cellulose hydrate fibers which have lengths ranging from about 30 mm to about 150 mm.

8. Equipment for carrying out a process for preparing swellable cross-linked carboxyalkylcelluloses by reacting cellulose, a carboxyalkylating etherifying agent, and a cross-linking agent in an aqueous alkaline medium, comprising:
(a) means for preparing and storing the aqueous alkaline reaction mixture,
(b) means for contacting fibers or textile sheet materials containing these fibers, having a base of cellulose hydrate or of natural cellulose or sheet materials in the form of films or sponge cloths composed of cellulose hydrate, with an ample quantity of the aqueous alkaline reaction mixture
(c) means for partially removing the reaction mixture from the fibers or sheet materials contacted therewith, so that at least the quantity required for reaction is still present,
(d) means for treating with heat energy the fibers, films or sheet materials containing the remainder of the aqueous alkaline reaction mixture for the purpose of the actual chemical reaction,
and connecting means between a to d.

9. Equipment according to claim 8 including an additional means preceding means b for pretreating an unreacted natural cellulose in the form of fibers or an unreacted cellulose hydrate in the form of fibers.

10. Equipment according to claim 8 including an additional means between means c and d for post-treating fibers of natural cellulose or of cellulose hydrate which contain the remainder of the aqueous alkaline reaction mixture.

11. Equipment according to claim 8 in which means b is a sieve drum washer and means d is a sieve drum drier or a sieve belt steamer.

* * * * *